(12) United States Patent
Rinner et al.

(10) Patent No.: US 6,221,077 B1
(45) Date of Patent: Apr. 24, 2001

(54) HUMAN SPINE FIXATION TEMPLATE AND METHOD OF MAKING SAME

(75) Inventors: James A. Rinner, Racine; Kevin K. Marchant, Kenosha, both of WI (US)

(73) Assignee: Beere Precision Medical Instruments, Inc., Racine, WI (US)

( * ) Notice: Subject to any disclaimer, the term of this patent is extended or adjusted under 35 U.S.C. 154(b) by 0 days.

(21) Appl. No.: 09/514,913

(22) Filed: Feb. 28, 2000

(51) Int. Cl.[7] .................................................. A61F 17/56
(52) U.S. Cl. ................................................. 606/102; 33/512
(58) Field of Search ............................... 606/53, 102, 86, 606/60, 61; 33/511, 512, 562, 483, 493

(56) References Cited

U.S. PATENT DOCUMENTS 4,807,370 * 2/1989 Trimble .................................... 33/562
5,799,407 * 9/1998 Powell ..................................... 33/483
5,938,662   8/1999 Rinner .

FOREIGN PATENT DOCUMENTS

575828 * 4/1924 (FR) ....................................... 33/493

* cited by examiner

Primary Examiner—Gene Mancene
Assistant Examiner—Eduardo C. Robert
(74) Attorney, Agent, or Firm—Arthur J. Hansmann

(57) ABSTRACT

A method and template for making a rod to be implanted into a human for affixing the patient's spine. The template and the method consist of a metal rod covered by a flexible sleeve and end plugs which are cemented into the sleeve ends to fluid tightly encase the rod and prevent particulates from getting into the patient.

9 Claims, 1 Drawing Sheet

U.S. Patent
Apr. 24, 2001
US 6,221,077 B1
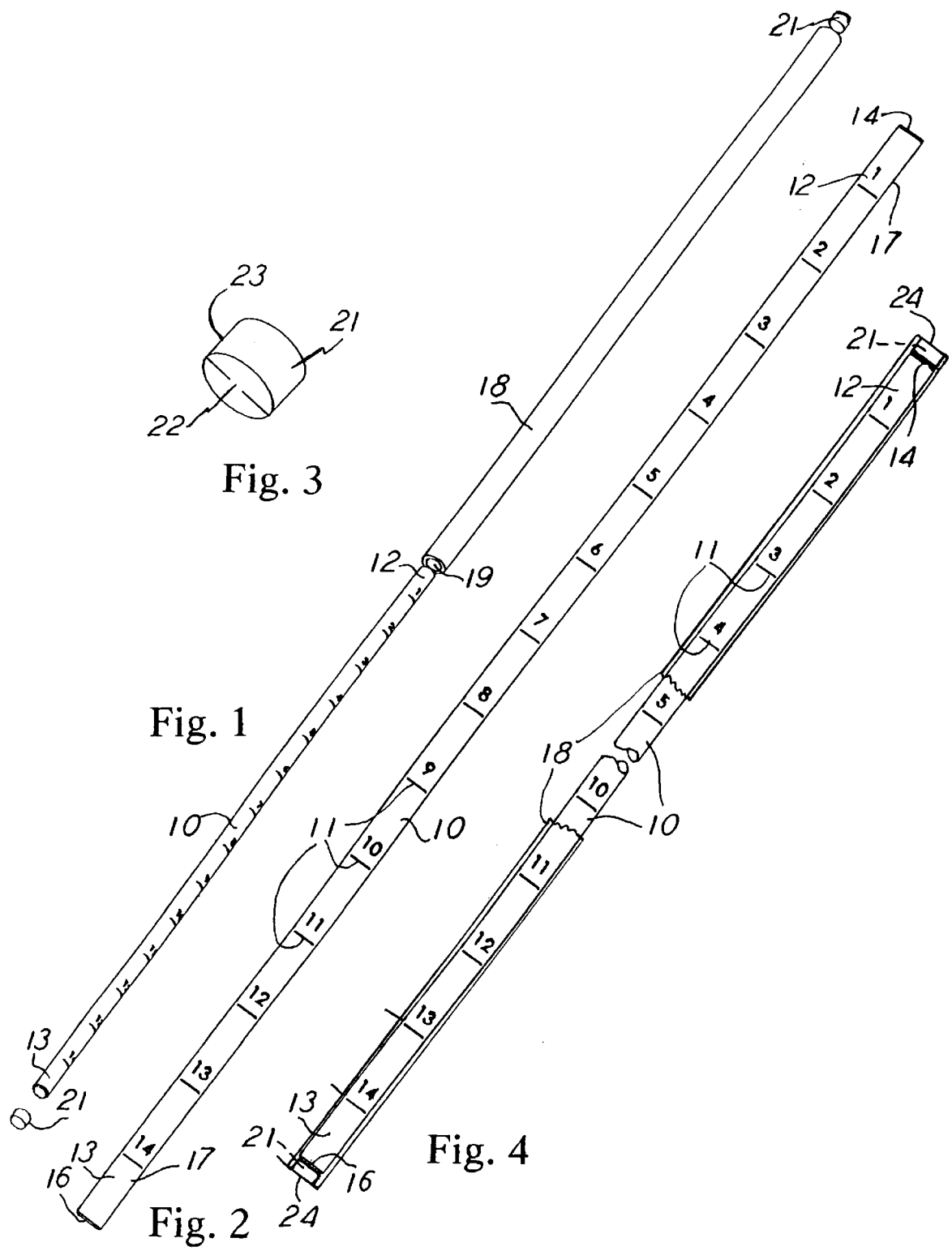

HUMAN SPINE FIXATION TEMPLATE AND METHOD OF MAKING SAME

This invention relates to a human spine fixation template and method of making same.

BACKGROUND OF THE INVENTION

In the medical arts, it is common practice to affix a rod to a patient's spine in order to immobilize the spine in its length adjacent the affixed rod. In that practice, the surgeon determines the necessary length and configuration of a rod which is to be implanted into the patient, and that determination is based upon utilizing a template rod which the surgeon initially configures to the shape of the length of the spine which is to immobilized. That is, the surgeon initially bends and measures a bendable rod to conform to the affected part of the patient's spine. That rod becomes a template rod which is then utilized for the configuring of another rod which is to be implanted into the patient and secured to a portion of the length of the spine.

In that practice, it is important that there be no foreign matter introduced into the patient, and thus the template rod should not be the source of any foreign matter deposited into the patient when the surgeon is configuring that template according to the shape of the patient's spine. However, a rod of a preferred material, such as aluminum, can release contaminating foreign particles into the patient's body when the rod is subjected to the forces and action of bending, and of course that is undesirable. The introduction of foreign particulates is a major danger and concern in the implantation of spinal rods.

Accordingly, the present invention provides a template rod assembly which does not release any foreign matter into the patient, that is, the assembly's own flakings and the like, when it is being configured or bent adjacent the patient's spine. To accomplish this objective in the present invention, the template rod of this invention is provided with a sleeve which covers the rod and thereby precludes release of the particulates of the rod material. Such sleeve is preferably made of a silicone material which can be snugly positioned over the rod, and two end plugs are utilized for snugly sealing the assembled rod and sleeve at the ends of the assembly. As such, the template rod is fully protected and can be bent without leaving any foreign particles in the patient.

The present invention also includes the method of accomplishing the aforementioned and to do so in a manner which provide a a protected template rod and does so in an efficient and reasonably cost-effective manner.

Still further, the assembled rod and sleeve of this invention present incremental length indicia affixed along the length of the rod so the surgeon can determine the overall length, as well as the location, for the bends of the template rod. With that information, the surgeon can then use the template to select a final rod and to bend the final rod to conform to the length and configuration of the template rod and then implant the final rod into the patient.

In accomplishing all of the foregoing, the present invention provides the coextensive length of an assembled rod and sleeve with two end plugs which extend within the respective opposite ends of the sleeve to render the entire assembly of the rod, sleeve, and the two end plugs fluid and particle-release tight, all so that no fluid nor particulate can pass to of from the interior of the assembly. In that regard, the present invention has the two end plugs snugly assembled with the sleeve. Also, the two plugs serve to indicate the respective incremental length of the assembly at its opposite ends so that the overall length of the assembly includes the end plugs, and those two end plugs conform to the opposite end length increments along the length of the assembly.

The sleeve is of a transparent material, and thus indicia of length measurement on the rod can be seen through the encasing sleeve. Also, the plugs can be made of the same material as that of the sleeve to thus be non-offensive to the patient where the material is silicone or the like.

The assembly of the three components of the rod and the sleeve and the two end pugs can be snugly assembled, as mentioned above, without the need of any tools or special skills.

BRIEF DESCRIPTION OF THE DRAWINGS

FIG. 1 is an exploded perspective view of all the parts in the assembly of the template rod of this invention.

FIG. 2 is an enlarged perspective view of the rod shown in FIG. 1.

FIG. 3 is an enlarged perspective view of one of the two end plugs in FIG. 1.

FIG. 4 is a fragment of an enlarged perspective view of the rod, the sleeve, and the two plugs in their assembled positions relative to their exploded positions of FIG. 1.

DESCRIPTION OF THE PREFERRED EMBODIMENT AND THE METHOD

There is a rod 10 which is preferably of aluminum material which can be bent by a surgeon's finger pressure while the rod is positioned adjacent the patient's exposed spine. As such, the configuration of the rod 10 along its length may have compound bends or several bends therealong to conform to the patient's spine which is ultimately to be immobilized or fixed by another rod which will be made according to the configuration of the template rod 10. As such, the procedure is standard and well known by those skilled in the art, and the final rod which is to be implanted is not shown herein, but, as mentioned, is well known to those skilled in the art.

The rod 10 has a longitudinal extent throughout its length, and it has the incremental distance markings with corresponding indicia, such as the numbers 1 through 14 as shown in FIG. 2. The indicia guides the surgeon in establishing the location of the bends for the purpose of finally formulating the final rod which is not shown herein. The rod 10 has the equally spaced indicia designated 11 disposed therealong.

The rod 10 extends between its opposite ends 12 and 13, and it is shown in straight, and thus non-bent configuration, throughout its length and along its longitudinal axis of its length. The rod 10 is of a cylindrical shape throughout its length and is of only one continuous cylindrical shape and cross-sectional diameter through its entire length. As shown, it is in the condition prior to when the surgeon shapes it to conform to a patient's spine to serve as a template rod. The rod 10 is formed by machining and it is annealed, and it can have a black anodized finish.

The distances between the consecutive markings between "1" and "14" are preferable all the same. However, the rod lengths from the markings "1" and "14" to the respective adjacent very ends 14 and 16 of the opposite ends of the rod 10 are each of a dimension less than the distances between the markings "1" and "14", and those lengths are designated 17. However, the end lengths 17 are more than one-half the distances between each two consective ones of the markings shown, and in fact, are approximately three-quarters the length of those distances between every two consecutive markings.

A tubular cover 18 is of a clear or transparent elastomer material such as silicone and it is of a length slightly longer than the length of the rod 10. Also, the cover 18 is a sleeve which slides over the rod 10 to snugly encase the rod 10 along its entire length. However, the markings are visible through the cover 18, as seen in FIG. 4. The interior diameter of the cover at 19 is substantially the same as the exterior diameter of the rod 10, so the cover 18 is snug on the rod 10 and will not slide therealong to a degree that it will tend to slide off the rod 10 when the rod 10 is subjected to forces of bending or the like.

Two end plugs 21 complete the assembly, and they are positioned as shown in FIG. 4. The plugs 21 are cemented into the assembly and are fluid tight with the sleeve 18 to thereby provide a completely enclosed casing for the rod 10. The plugs are of a cylindrical shape with a diameter designated at 22 and that is substantially the same size as the interior diameter 19 of the sleeve. Also, the plugs are of an axial length designated at 23. As mentioned, the length of each rod end 12 and 13 from the adjacent marking 11 at the respective end 12 and 13 is less than the distance between consecutive markings 11, and the plug length 23 and the rod length 12 or 13 together are respectively of the length which is the same as that between the consecutive markings 11. That is, the respective lengths of the rod ends 12 and 13, along with the respective plug lengths 23, present the exact distance as that between the consecutive markings 11. Thus, the assembly has the uniform distances between the consecutive markings 11 and also between the markings "1" and "14" and the assembly respective ends, as designated 24.

FIG. 4 fragmentarily shows the assembly and the features of the encasement, the cemented positioning of the plugs, and the uniformity of the distances between the markings along the entire assembly and completely to the assembly ends 24. No metal parts are required to form the encasement which consists only of the sleeve 18 and the two plugs 21.

Throughout this description, the method is also described and disclosed to one skilled in the art, and it is a part of this invention. The sleeve is stretched over the rod 10 and the ends of the sleeve extend beyond the respective ends of the rod to provide a cylindrical cavity at each end. The plugs can be of silicone material and glue is applied to them and they are then inserted into the respective sleeve cavities and form a fluid-tight bond with the sleeve. There could be a length of the plug material in the form of a cylindrical rod of a length greater than that of each plug, and an end of that rod could have glue applied thereto, and the rod, along with the glued end, could then be maneuvered to have the plug inserted into its cavity in the sleeve. The surplus and protruding remainder of the rod could then be cut off, leaving the cemented plug in its place.

With the template and its bent configuration as formed by the surgeon, the final rod or fixation member can be configured in accord with the incremental markings displayed along the template, and bending can be done manually or with tool assist. The assembly provides a template rod which is flexible throughout its entire length and it is soft and resilient throughout its length. It will not press upon the patient's body to cause damage thereto. Also, it can be bent at the ends of the assembly because there is no rigidity at the ends.

What is claimed is:

1. A method of making a template for use in implanting a rod into a person's body for skeletal support, comprising the steps of:

forming an elongated template rod of rigid but configurable bendable material capable of holding a bent configuration imposed thereon and having a length with two terminal ends spaced apart a selected first distance and having a uniform cross sectional size throughout said length, applying a plurality of markings onto said template rod in equal increments of spacing between said markings to thereby indicate equal distances between every two of said markings along said template rod, forming a sleeve of elastomer and transparent material and having two terminal ends spaced apart a distance slightly greater than said first distance and having an open interior cross sectional size the same as that of said template rod throughout the length of said sleeve, joining said template rod and said sleeve together to have said sleeve completely encase and cover said template rod and have said respective terminal ends of said sleeve extend equally beyond said terminal ends of said template rod and thereby provide an open space of a given size within said terminal ends of said sleeve, and forming two end plugs each of a solid mass and of an overall size only that of said given size and placing said plugs into each respective said space to fully occupy said space and with all of each of said plugs being fully within and enclosed by said sleeve and be completely snug with the interior of said sleeve to thereby present a seal relative to said template rod, all thereby being arranged to prevent the passage of any material from said template rod to beyond said sleeve and each of said plugs.

2. The method of making a template as claimed in claim 1, including the steps of forming said template rod and said sleeve and said plugs to be circular in their cross sections transverse to said length and with the external diameters of said template rod and said plugs and the interior diameter of said sleeve all being the same.

3. The method of making a template as claimed in claim 2, wherein said template rod and said sleeve are shaped to form an assembly which is arranged to be of a cylindrical shape and of a single circumferential size throughout said length of said assembly.

4. The method of making a template as claimed in claim 1, including the step of applying glue to said plugs prior to inserting said plugs into said spaces.

5. The method of making a template as claimed in claim 1, wherein said sleeve and each said plug are made of silicone material and are transparent.

6. The method of making a template as claimed in claim 1, wherein the length of each said plug and each said space are the same and each said plug is positioned to extend spaced a dimension from an adjacent one of said markings whereby the total extent of said same length and said dimension are equal to said increments of spacing between said markings.

7. A template for use in making a spine-fixation rod for use in human implant comprising a template rod made of a material which is arranged to be capable of bending in response to force exerted by a user's fingers and which is capable of retaining a bent shape and which has a length and a terminal end at the two extremes of said length, said template rod having equal increments of markings spaced along said length of said template rod, a cylindrical sleeve made of a transparent elastomer material and having two ends and being snugly disposed on said template rod and with said sleeve ends extending beyond said template rod terminal ends and thereby presenting an open space at each said terminal end, a plug snugly disposed in each said space at each said terminal end of said template rod and being fully enclosed by said sleeve and with said template rod and said sleeve and said plugs forming an assembly which is sealed to preclude movement of any said template rod material beyond said assembly, and each said plug having a length extending co-axially with said template rod and with each said plug length terminating a spaced distance from an adjacent one of said markings and with said length of each said plug and said spaced distance from said adjacent marking being of a total extent along said rod length to equal the increment between every two of said markings.

8. The template as claimed in claim 7, wherein each said plug is glued onto said sleeve in each respective said space.

9. The template as claimed in claim 8, wherein said sleeve and each said plug are of elastic silicone material and transparent.

\* \* \* \* \*